United States Patent
Spina et al.

(10) Patent No.: US 8,999,355 B2
(45) Date of Patent: Apr. 7, 2015

(54) NON-RINSE OFF COSMETIC COMPOSITION AND A COSMETIC PRODUCT COMPRISING SAID COMPOSITION

(75) Inventors: Marcos Rogério Spina, Jundiaí (BR); Cristiane Regina Carnelos, Tatuapé (BR); Claudia Leo, Brooklin Novo (BR); Luciana Faria, Jandira (BR)

(73) Assignee: Natura Cosmeticos S.A., Sao Paulo (BR)

( * ) Notice: Subject to any disclaimer, the term of this patent is extended or adjusted under 35 U.S.C. 154(b) by 1712 days.

(21) Appl. No.: 11/910,495

(22) PCT Filed: Apr. 4, 2006

(86) PCT No.: PCT/BR2006/000063
§ 371 (c)(1),
(2), (4) Date: Apr. 7, 2008

(87) PCT Pub. No.: WO2006/105628
PCT Pub. Date: Oct. 12, 2006

(65) Prior Publication Data
US 2008/0193396 A1    Aug. 14, 2008

(30) Foreign Application Priority Data
Apr. 4, 2005    (BR) ...................... 0501569

(51) Int. Cl.
*A61K 8/36* (2006.01)
*A61K 8/37* (2006.01)
*A61Q 1/04* (2006.01)
*A61Q 1/06* (2006.01)
*A61Q 19/00* (2006.01)

(52) U.S. Cl.
CPC ................. *A61K 8/361* (2013.01); *A61K 8/375* (2013.01); *A61Q 1/04* (2013.01); *A61Q 1/06* (2013.01); *A61Q 19/00* (2013.01)

(58) Field of Classification Search
None
See application file for complete search history.

(56) References Cited

U.S. PATENT DOCUMENTS

| | | | |
|---|---|---|---|
| 5,849,315 A | 12/1998 | Rerek et al. | |
| 6,225,485 B1 * | 5/2001 | Bertz et al. | 554/148 |
| 6,303,105 B1 * | 10/2001 | Shah et al. | 424/61 |
| 2004/0120913 A1 * | 6/2004 | Shah et al. | 424/70.12 |
| 2006/0127332 A1 * | 6/2006 | Rodrigues et al. | 424/63 |
| 2007/0092462 A1 * | 4/2007 | Gans Russ et al. | 424/64 |

FOREIGN PATENT DOCUMENTS

| | | |
|---|---|---|
| EP | 1 228 747 | 8/2002 |
| JP | 2003206213 A * | 7/2003 |
| JP | 2004051517 A * | 2/2004 |

OTHER PUBLICATIONS

Translation of JP 2003206213 A, Jul. 2003.*
Translation of JP 2004051517 A, Feb. 2004.*
Moore et al. (Household & Personal Products 2006; 7 pages).*
International Search Report for PCT Application No. PCT/BR2006/00063; Filed Apr. 4, 2006; Date of Completion Aug. 8, 2006; Date of Mailing Sep. 11, 2006.
Written Opinion for PCT Application No. PCT/BR2006/00063; Filed Apr. 4, 2006; Date of Completion Aug. 8, 2006; Date of Mailing Sep. 11, 2006.
Response to Written Opinion Dated Feb. 2, 2007.
International Preliminary Report for PCT Application No. PCT/BR2006/000063; Filed Apr. 4, 2006.

* cited by examiner

*Primary Examiner* — Ernst V Arnold
(74) *Attorney, Agent, or Firm* — Alston & Bird LLP

(57) ABSTRACT

The present invention relates to a non-rinse-off cosmetic composition that provides to the skin, especially the lip skin, a hydrating and restoring action. More specifically, the invention relates to a non-rinse-off cosmetic composition particularly usable on the skin in the region of the lips, which comprises ricinoleyl monomaleate triglyceride and palmitic acid. Further, the present invention relates to cosmetic products comprising the cosmetic composition described above.

16 Claims, 3 Drawing Sheets

NON-RINSE OFF COSMETIC COMPOSITION AND A COSMETIC PRODUCT COMPRISING SAID COMPOSITION

FIELD OF THE INVENTION

The present invention relates to a non-rinse-off cosmetic composition that provides a moisturizing and restoring action on the skin of the lip regions.

DESCRIPTION OF THE PRIOR ART

Color the lips to get sensuality is a habit practiced by women since the Ancient World. In that time, the only choice was to resort to natural products. In Egypt, the young ladies used "Tyrian purple", while the Greek ones used to apply a red root called "polderos" with honey cerate, to give their mouths a more pleasant and moist aspect.

Since then, the use of lipstick has become popular and has gone through various moments and modes, alternating discreet and indiscreet models. But the seduction of lipstick as we know it today has invaded the consumption society in the Twenties, when the versatile and practical stick was invented.

The lipstick is an indispensable complement and is on the lips of most women. However, it is not only because it confers beauty and sensuality, but rather because of the benefits which the modern formulas can bring to the lips, making them more sensual and healthy.

The size, the curvature and the eversion of the lips vary in men and in women, as well as in the ethnical populations. The lips are different from other tissues of the human body. The lips are a transition tissue, an evolutionary combination of the facial skin and of the buccal membrane. This combination is unique, since, unlike the skin or the mouth, the lips do not have a natural defense mechanism. The only protection comes from the touch of saliva by means of the tongue or pressing the lips against each other against an external threat.

The transactional nature of the lips suggest that, anatomically speaking, the lip area does not enjoy the complete functionalities, as is the case of the epidermis or the buccal mucosa. Since the thickness of the *stratum corneum* (the outermost layer of the skin) is thinner and the number of keratinized cells is smaller, the lips have a reduced effective natural protection, but a higher absorption capacity. However, any active ingredient present in products for lips, should have a substantial absorption.

The lip tissues do not have a moisturizing capacity due to the non-existence of sebaceous or salivary glands. For this reason, the lip tissues are subject to natural dryness. In spite of this, moisture can be applied to the lips if the lip product contains active substances that stimulate the regeneration of the cells and that maintain water under the surface of the lips.

There is little or no melanin in the lip tissues. This means that there will be less or no absorption of ultraviolet rays (UV), which entails a greater susceptibility to damages to the cells.

The lip tissues have vascularization close to the surface, creating a red or pink color. This superficial vascularization also produces a stronger impact on the metabolism of the surface cells.

The lips also have a large number of nerve endings. This means a superior sensitivity to dryness or damages. The lips are subject to several of diseases, which require the use of safe unctuous raw materials for the development of a formula. Some of the most common complaints about the lips are: dryness, cracked lips, redness and cracking, aphthae, lip cancer and lip wrinkles.

Dryness and cracking are related with the loss of natural moisture of the lips. Redness and cracking are due to a sensitivity reaction of chemical products and pollutants. Aphthae or fever blisters are clinically related with the herpes simplex virus, being caused by a drop in the immune system and due to sunburns, excess dryness, disease and stress. The exposure to sunlight may cause folds on the lips. The treatment requires hydration and restoration of glycosaminoglycans, together with natural collagen.

Since the lips are one of the parts of the body that are most exposed to external aggressions and also because they have a different texture from the rest of the skin, they require special care. The great enemies of the lips are: sunlight, wind, cold, that is to say, in any season of the year or at any temperature there is a great possibility of the lips becoming parched.

The applicant indicates hereinafter the relevant prior-art documents related with the matter of the present invention.

Document U.S. Pat. No. 6,225,485 discloses a compound obtained by means of the reaction between castor oil and a cyclic carboxylic acid anhydride. The use of this compound is indicated in products for personal care, the use thereof being foreseen in exclusively rinse-off products. Further, the process of obtaining this compound is also disclosed.

Document EP 1,228,747 describes a cosmetic formulation comprising a plurality of spheres having a hydrated volume. This composition may be added to formulations of products such as lipsticks and has long duration when applied.

Document WO 02/58642 discloses structural compositions comprising one or more liquid oily phases that contain at least one fat-soluble ester without hydroxyl groups, wherein at least one ester is not derived from castor oil. Among the examples of products cited in this document, lipstick is mentioned.

Document DE 3841784 describes a modified castor oil in which the viscosity has been increased by heating. This oil may be added to cosmetic compositions, acting as an oily component and may further be used as a lubricant for lipsticks.

Document U.S. Pat. No. 6,174,533 discloses topical compositions that provide coverings for skin imperfections, as for example pores and uneven skin tone. The compositions contain a particulate titanium-oxide material. It may be applied for the treatment of the lips in the form of lipsticks. One of the components that may be added to the formulation of these compositions is coconut ricinoleyl alcohol.

From the description of the present invention hereinafter, it follows that no teaching of the prior art proposes advantages referring to prolonged moisturizing and to restoration of the skin provided by the use of lipstick or lip product.

SUMMARY OF THE INVENTION

The invention relates to a non-rinse-off cosmetic composition, particularly usable on the skin of the lip region, which comprises ricinoleyl monomaleate triglyceride and palmitic acid.

The invention further relates to cosmetic products comprising the cosmetic compositions aimed at above.

BRIEF DESCRIPTION OF THE FIGURES

The present invention will now be described in greater detail with reference to the figures that illustrate the performance tests of the present invention.

DETAILED DESCRIPTION OF THE INVENTION

Figure 1:
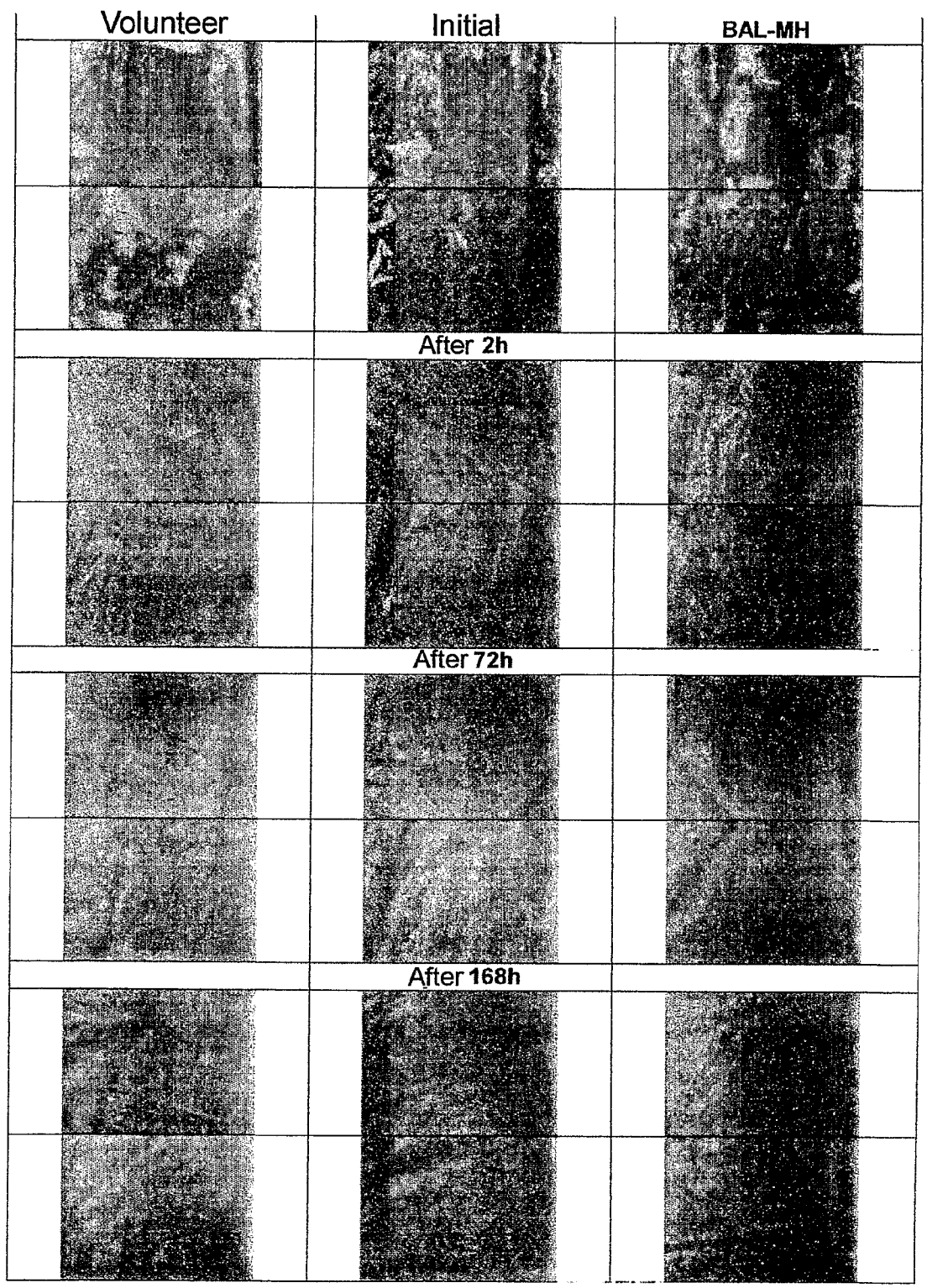
FIG. 1 illustrates the evolution of the efficacy of the composition represented in the example 1.1 of the present invention, applied to lips with regard to the attributes of restoration and uniformization of the local texture of the skin.

The present invention describes a non-rinse-off cosmetic composition that provides moisturizing and restoration to the lips and regions adjacent this area. In other words, the composition of the present invention meets the cosmetic requirements, so that the user, upon applying the product to the lip region, will feel his/her lips more moisturized.

The development of the cosmetic composition of the present invention was based on the skin-moisturizing systems. Substances that exhibit a synergistic effect were added, providing hydration and restoration of the skin in the lip region. In this way one has obtained a composition intended specially for the lip region, which exhibit substantivity with the skin of this region and further causes the formation of a lamellar gel, which will be explained in greater detail later.

Mechanisms of Skin Hydration

In short, moisturizing means supplying water to the skin and still create on it the condition of retaining the available water. The retention of water is achieved by various different mechanisms.

1) Humectancy: applying to the skin a hygroscopic, humectant substance. By their physicochemical characteristics, these molecules keep attached to various molecules, which would be lost under normal circumstances;

2) Occlusion: waxy and oily substances are more impermeable to water and, when applied to surfaces, tend to prevent excess loss of water. If this loss is excessive, the skin will become dried;

3) Replacement of lipids: it consists in applying physiological lipids, mainly fatty acids, cholesterol and ceramides. These lipids are become integrated into the normal physiology of the skin and starts to be part of the hydrolipidic barrier located in the deepest layers of the Stratum Corneum (SC);

4) Sensorial property/Re-greasing: strictly speaking, this is not a moisturizing mechanism; however, in subjective analyses, the users tend to consider a product to be a well moisturizing one if a small amount of oil improves the skin emollience. This "feeling of hydration" is important when skin-cleaning products such as makeup removers, toilet soaps and lipsticks are evaluated; and 5) Active Hydration: emulsions—products intended to promote skin hydration, such as creams or lotions, the lipid phase of which promotes occlusion and the aqueous phase of which has hygroscopic ingredients that provide humectation.

Below, we present a table showing all the hydration mechanisms that actuate in the composition of the present invention, resulting in maximum moisturizing of the lips of the consumer.

| Hydration mechanisms | Components |
| --- | --- |
| Replacement of lipids | Cupuaçu butter and Ricinoleyl monomaleate triglyceride (RMT) |
| Humectancy | Cupuaçu butter |
| Occlusion | Waxes and film formers |
| Active hydration | Hydraspheres |
| Sensorial properties (softness, smoothness, texture) | Emollients |

The main examples of products that can be prepared from the non-rinse-off cosmetic composition of the present invention are:

Lipsticks in their different applications;
Non-rinse-off emulsions for the skin;
Makeup products for face and lip skin;
Products for protection of face and lip skin;
Gloss in its different applications;
Balms, sticks and lip protectors;
Among other products for the lip area.

The non-rinse-off cosmetic composition of the present invention has a variety of advantages and characteristics desired in a product for the skin, some of which are listed below.

1. the composition of the present invention provides moisturizing to the lips, that is, humectancy, occlusion, replacement of lipids, besides providing regreasing of the skin. These properties prove to be more intense than those provided by similar products of the prior art;

2. this composition confers to the skin moisturizing, softness, smoothness properties, besides exhibiting a creamy texture;

3. the composition of the present invention provides restoration of the skin;

4. it is stable;

5. it exhibits an adequate texture during the application;

6. it is easy to spread;

7. it has a high capacity of maintaining skin hydration;

8. it does not cause any kind of adverse reaction or skin injury;

9. it is compatible with a variety of actives;

10. it exhibits appropriate chemical stability;

11. the association of RMT and palmitic acid mimetizes the formation of a structure that resembles the gel lamellar structure formed naturally on the skin. With the formation of this gel, there is greater substantivity of the non-rinse-off product with the skin, thus enabling greater actuation of the actives and retention of water;

12. the compound RMT present in the composition of the present invention interacts with the skin, when the product is applied to this substrat, the formation of a protecting layer is observed;

13. the compound RMT by be a castor-oil derivative, acts on the structure of the lipstick core, making it more resistant in its structure and more emollient upon application.

Non-Rinse-Off Cosmetic Composition

The non-rinse-off cosmetic composition of the present invention is particularly usable on the skin of the lip region and comprises ricinoleyl monomaleate triglyceride and palmitic acid, which are components insoluble in water and tend to last longer on the skin than, for example, rinse-off compositions such as liquid toilet soaps.

The association of said RMT (ricinoleyl monomaleate triglyceride) and palmitic acid mimetizes the formation of a structure that resembles the lamellar structure formed naturally on the skin, especially in the lip region. With the formation of this gel, there is greater substantivity of the non-rinse-off product with the skin, thus enabling greater actuation of the actives and retention of water, achieving an improved hydration and restoration of the skin.

According to the teachings of the prior art, the use of RMT in cosmetics was exclusive of rinse-off products, with application in personal care. So, its potential of hydrating and restoring the skin was not verified, since it was removed with the action of water, for instance, when the user made his/her personal hygiene. Thus, the present invention presents the use of the compound RMT for essentially cosmetic purpose.

This composition comprises components that, when combined, exhibit a synergistic effect, resulting in a maximized moisturizing action and restoration of the lip skin.

This cosmetic composition may further contain several components, such as agents, that provide occlusion, like waxes and film formers, components that act on active hydration like hydraspheres, sensorial-property modifiers like emollients, beside photo protectors (sunscreens) and other agents that have specific functions required for each composition necessary for each situation, such as: thickening agents, preservative agents, wetting agents, dyes, oiliness adsorbing agents, actives, anti-aging agents, among others.

The following components present in the non-rinse-off cosmetic composition of the present invention are described hereinafter.

Ricinoleyl Monomaleate Triglyceride

This compound, commercially known as Ceraphyl RMT®, produced by ISP (International Specialty Products), acts on the skin simulating the structure of the ceramides and cholesterol found in nature and that act as barriers in retaining water.

The RMT molecule has been synthesized by reacting maleic anhydride with a castor-oil derivative and has the following formula:

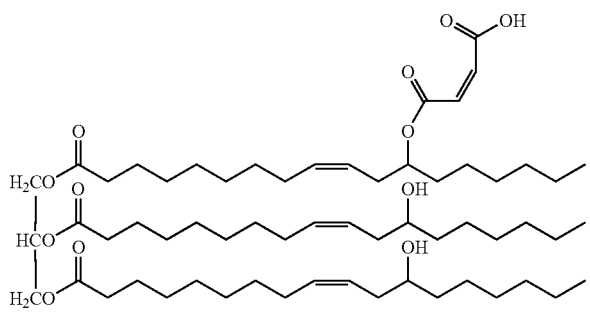

The lipids present in the stratum corneum (EC) are located in the healthy skin in the form of crystalline lamellar gel; this gel has the function of a barrier and prevents skin dehydration.

In the stratum corneum (EC), the ceramides and cholesterol act in conjunction and guide the lipids to form the crystalline lamellar gel. Therefore, ingredients that stimulate or form this natural lamellar gel present in healthy skins can bring many benefits as far as skin regeneration and hydration are concerned.

In vitro tests showed that the RMT molecule associated to palmitic acid form a lamellar structure very similar to the lamellar gel structure that is naturally present in healthy skins.

Then, in the non-rinse-off cosmetic composition of the present invention, RMT interacts with the palmitic acid that is present, for instance, in Cupuaçu butter, mimetizing the crystalline gel.

Preferably, RMT will be added to the cosmetic composition of the present invention in excess. So, the excess may react with the lipids of the skin and form the lamellar gel again.

Bench tests have shown that, applying pure RMT onto the skin and spreading it naturally, it will interact with the skin, showing the formation of a protective layer.

The lamellar gel formed by the RMT structure exhibits great substantivity with the skin, providing the benefits of restoring and moisturizing.

Therefore, RMT acts on the lip skin, forming a lamellar gel similar to the one that is naturally present in the stratum corneum. This gel has the function of a barrier and prevents water evaporation. It provides prolonged hydration due to the formation of a resistant film. Therefore, it is one of the compounds that act on the hydration and restoration mechanisms.

The minimum amount of RMT that should be added to the composition of the present invention must follow the ratio 1:1 with the amount of palmitic acid. Preferably, excess RMT is added.

In the preferred embodiments, Ricinoleyl Monomaleate Triglyceride is added in an amount ranging from 0.01% to 15.00%, preferably from 1.0% to 10.0%, more preferably from 2.0% to 7.0% by weight, based on the total weight of the composition.

Palmitic Acid

Preferably, cupuaçu butter is used as a source of palmitic acid present in the composition of the present invention. Cupuaçu butter further provides a silky sensorial effect, provides retention of moisture and is composed by fatty acids that help in recovering the skin.

In the non-rinse-off cosmetic composition of the present invention, Ricinoleyl Monomaleate Triglyceride interacts with the palmitic acid present in the cupuaçu butter, simulating the crystalline gel when applied to the skin.

The amount of cupuaçu butte to be added to the composition of the present invention should be effective to comprise the necessary amount of palmitic acid.

Further, the cupuaçu butter comprises oleic acid and linoleic acid, which have the ability of protecting and restoring the skin from the damages and burns caused by the sun-rays.

Moreover, cupuaçu butter comprises calcium and magnesium, components that act in hydrating, protecting against early aging and vitality. Calcium and magnesium participate in the cellular metabolism and regulate numberless physiological mechanisms, and on the skin they also act in the process of forming the cutaneous barrier. In addition, they play a fundamental role in forming this barrier, stimulating the cells to produce more natural cement. In this way, the stratum corneum becomes strong and performs better its barrier function. These two nutrients help the skin to maintain and recover its hydration naturally.

Thus, calcium and magnesium, present in cupuaçu butter, potentiate the skin restoring and hydrating system.

Further, cupuaçu butter contains sugars, starch and pectin, which provide absorption and retention of water, increasing the moisturizing potential. Alternatively, Shea butter may be used.

In the preferred embodiments, cupuaçu butter is added in an amount ranging from 0.1% to 20.0%, preferably from 1.0% to 10.0%, more preferably from 1.5% to 8.0% by weight, based on the total weight of the composition.

The components described hereinafter are preferred components to be added to the cosmetic composition of the present invention.

Hydraspheres

These are marine collagen microspheres, dehydrated and with a very small diameter, which enables them to penetrate the skin as far as the stratum corneum. Upon reaching this layer, they become rehydrated by capturing the water that the skin would be losing, keeping it hydrated. After this rehydration, they return to their original diameter, filling up small lines, making them smooth.

In the preferred embodiments, hydraspheres are added in amounts ranging from 0.01% to 5.00%, preferably from 0.05% to 3.00%, more preferably from 0.1% to 1.0% by weight, based on the total weight of the composition.

Agents that Modify Sensorial Properties

First, one understands by "sensorial" the set of properties that provide softness, smoothness and adequate texture.

In this regard, some components may be added to the composition of the present invention. By adding the preferred components cited below, one obtains a sliding product, which provides softness with good covering of the substrate and still reinforces the feeling of hydration on the lips.

Some examples of preferred sensorial modifying agents to be added to the composition are:
mineral, vegetable and synthetic waxes;
liquid and solid polymers;
rheology agents;
esters with carbon chain of different sizes;
alcohols.

In the preferred embodiments, a combination of waxes, esters and polymers is added in an amount ranging from 50.0% to 95.0%, preferably from 55.0% to 90.0%, more preferably from 60.0% to 85.0% by weight, based on the total weight of the composition.

Film Forming Agents

This component of the cosmetic composition of the present invention provides the formation of a film that adheres to the skin, retaining the water molecules under it, guaranteeing skin hydration.

In order for the application of this product not to cause any irritation on the skin, one should use compounds that are dermatologically inert, that is to say, compounds that do not cause hypersensitivity and are not toxic and still remain on the skin surface, thus not penetrating it.

Preferably film-forming agents to be added to the composition of the present invention are: glyceryl abietate, glyceryl rosinate, variants and derivatives thereof and mixtures thereof.

The ingredients glyceryl abietate and glyceryl rosinate act to form a film, beside providing gloss to the lips, adherence to the skin and retention of water under the skin, formation of film and provides adherence to the skin.

Alternatively, other film forming agents may be added, as for example, polyvinylpyrrolidone derivatives, silicone derivatives, polyurethane derivatives, film-forming polymers and ingredients that provide film formation adherent to the skin.

In the preferred embodiments, a combination of glyceryl abietate and glycerin rosinate is added in an amount ranging from 0.1% to 15.0%, preferably from 1.0% to 10.0%, more preferably from 1.5% to 7.0% by weight, based on the total weight of the composition.

Pigments

Pigments may be added to the composition of the present invention for the purpose of providing various tonalities.

Some examples of preferred pigments to be added to the composition are: inorganic pigments, organic pigments, synthetic pigments, brilliant pigments, covered pigments, provided that the concentrations allowed for use in the region to which the final product is intended are respected.

Sunscreens

In order to filter ultraviolet rays from solar radiation, sun protection agents are added.

Some examples of sunscreens that absorb ultraviolet rays, which are indicated to be added to the cosmetic composition of the present invention are physical and chemical fat-soluble or dispersible sunscreens indicated for the lip region.

In the preferred embodiments of the present invention, for products of topical application one uses, as a sunscreen system, the mixture of 2-ethylexyl p-methoxy cinnamate, benzofenone-3 and micronized titanium dioxide. In this regard, it is added:

benzofenone-3 in an amount ranging from 0.1% to 5.0% by weight, preferably from 0.5% to 4.0% by weight, more preferably from 1.0% to 3.0%;

2-ethylexyl p-methoxy cinnamate in an amount ranging from 0.1% to 10.0% by weight, preferably from 1.0% to 8.0% by weight, more preferably from 2.0% to 7.0%;

micronized titanium dioxide in an amount ranging from 0.1% to 8.0% by weight, preferably from 1.0% to 6.0% by weight, more preferably from 2.0% to 4.0%;

all the amounts being based on the total weight or the composition.

Other Optional Components

In order to impart to the non-rinse-off cosmetic composition of the present invention some desirable characteristic that is not achieved with the already cited components, optional components that are compatible with its properties. Some of these compounds that may be added to said compositions are:

active principles: vitamin E acetate, lycopene extracted from tomato, sunflower-seed extract, glycerin, lectin, grapeseed extract, α bis-abolol (anti-inflammatory active), D-pantenol, among others (conditioning active);

emollients: ethylexyl palmitate, isopropyl palmitate, capric/caprillyc triglyceride, octyidodecanol, glyceryl ricinoleate, cetyl ricinoleate, cetyl lactate, butters, among other esters, alcohols and oils;

silicones and variations thereof;

aromas;

glycolic plant extracts: chamomile, rosemary, thyme, calendula, carrot extract, common-juniper extract, gentian extract, cucumber extract, among others.

EXAMPLES OF COMPOSITION

The following examples are preferred variations of the non-rinse-off cosmetic composition of the present invention and should not be construed as limiting it. In this regard, it should be understood that the scope of the present invention embraces other possible variations, being limited only by the contents of the accompanying claims, which include the possible equivalents.

Example 1

Moisturizing Lipstick

1—Mass for Moisturizing Lipstick

| Components | Massic amount (%) |
|---|---|
| Candelilla wax | 5.86 |
| Carnauba wax | 2.64 |
| Microcrystalline wax | 5.86 |

-continued

| Components | Massic amount (%) |
|---|---|
| Polybutene | 7.32 |
| Pentaeritryl tetraisostearate | 7.76 |
| Ricinoleyl maleate triglyceride | 7.32 |
| Triberenin | 4.39 |
| BHT | 0.05 |
| Polyethylene | 5.86 |
| Propylpareben | 0.10 |
| Glyceryl rosinate and octyldodecyl miristate | 4.39 |
| Glycerol abietate | 0.73 |
| Gel GTCC V bentone/Isononyl isonoate | 36.74 |
| Cupuaçu butter | 1.46 |
| Ceteraryl meticone | 9.52 |

1.1—Colorless Moisturizing Lipstick

| Components | Massic amount (5%) |
|---|---|
| Mass for moisturizing lipstick | 87.90 |
| Benzofenone-3 | 2.00 |
| Dispersion in castor-bean oil of titanium, aluminum dioxide, simeticone | 2.50 |
| Ethylhexyl methoxycinnamate | 4.50 |
| Tocopheryl acetate | 1.00 |
| Aroma | 2.00 |
| Marine biopolymer spheres | 0.10 |

1.2—Moisturizing Lipstick

| Components | Massic amount (%) |
|---|---|
| Mass for moisturizing lipstick | 65.0-85.0 |
| Dispersion in castor-bean oil in a pool of pigments | qsp 100 |
| Benzofenone-3 | 2.00 |
| Dispersion in castor-bean oil of titanium, aluminum dioxide, simeticone | 2.50 |
| Ethylhexyl methoxycinnamate | 4.50 |
| Tocopheryl acetate | 1.00 |
| Aroma | 2.00 |
| Marine biopolymer spheres | 0.10 |

Tests—The Tests were Carried Out in External Institute
1. Test for Efficacy of Restoration and Uniformization of the Texture, Carried Out in External Institute This test has the objective of evaluating the efficacy of the composition of the present invention applied to the lips for the attributes of restoration and uniformization of the local texture of the skin, by capturing images by CCD micro camera and analysis of images via specific software.

In this test, two products described in examples 1.1 and 1.2 were analyzed.

20 volunteers with 18 to 60 years of age, who exhibited characteristics of drying, cracking or scaling of the lips, were selected. The exclusion criteria comprised the history of allergic reactions, diseases of the skin, and pregnancy or breast-feeding.

The study was based on the comparison of two groups of 10 volunteers distributed at random for the use of product 1 and of product 2.

The basal images were taken on the first day, after acclimatization and before application of the product. Then images were taken 2 hours after application of the product. Subsequently, new evaluations were made after 72 hours 168 hours from the routine use of the product.

Figure 2:
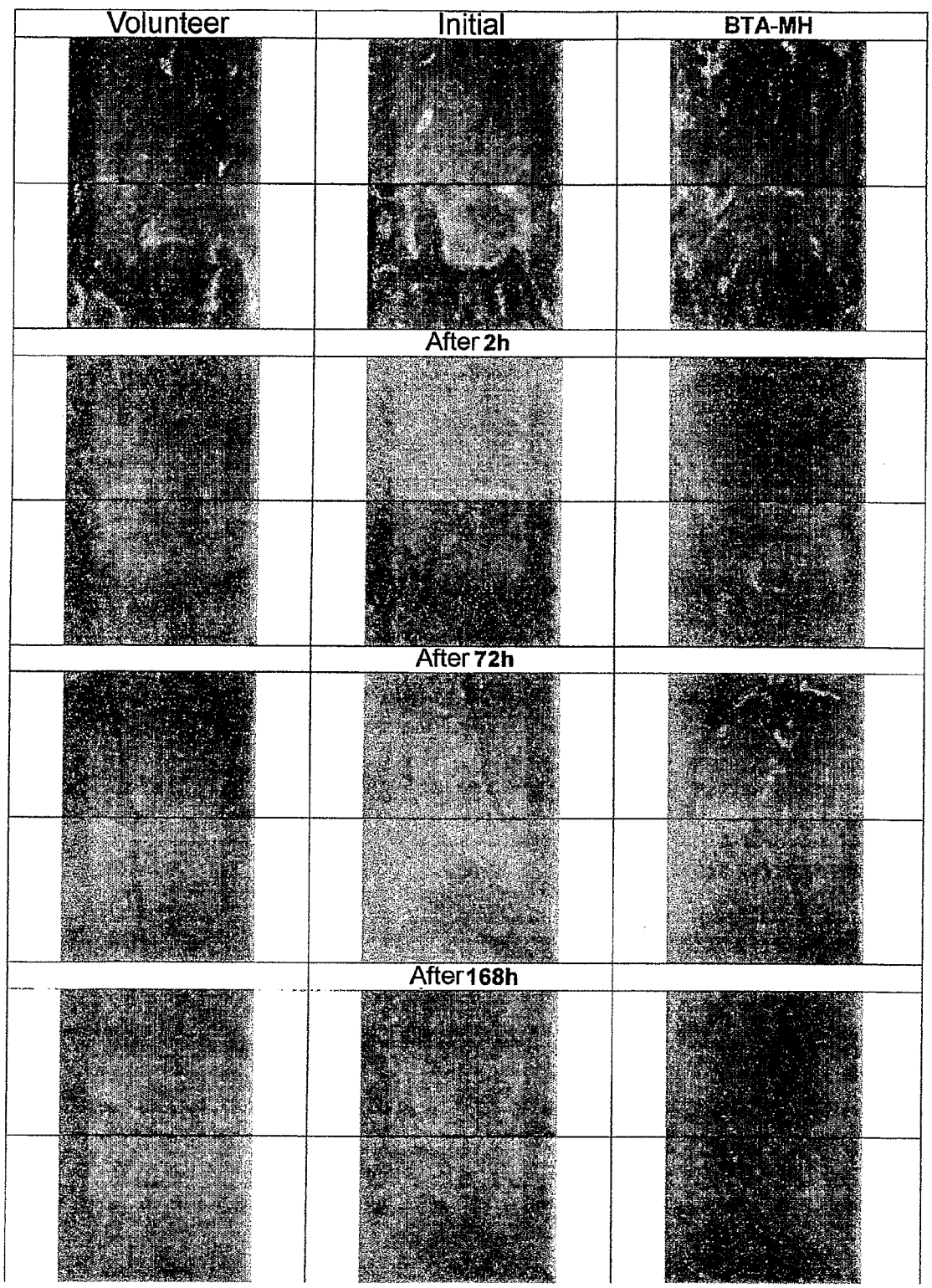
FIG. 2 illustrates the evolution of the efficacy of the composition represented in the example 1.2 of the present invention applied to lips with regard to the attributes of restoration and uniformization of the local texture of the skin.

Result: in both cases there was a positive evolution in the effect of the products with respect to the reduction of the lip damages, that is to say, lip restoration ranging from 38% to 54%. Examples of these results can be seen in FIGS. 1 and 2 that illustrate, respectively, the evolution of the efficacy of the composition of the present invention (examples 1.1 and 1.2, respectively), applied to the lips when for the attributes of restoration and uniformization of the local texture of the skin on two volunteers selected at random.

2—Skin-Evaluation Test by Means of FTIR-ATR

This test has the objective of evaluating the skin structure by means of ATR—Attenuated Total Reflectance for examination of the skin after the treatment with the cosmetic product, characterizing the hydration property conferred by application of lipsticks.

In this test, two products described in examples 1 and 2 were analyzed. Further one considered a control lipstick and a lipstick known from the market and that does not contain RMT in its composition.

20 volunteers with 18 to 50 years of age, who had characteristics of drying of the skin, were selected. The exclusion criteria comprised the history of allergic reactions, diseases of the skin and pregnancy or breast-feeding.

On each volunteer six sites were demarcated, three of them on each forearm. On each forearm, a site remained without application of any product. The products were applied at random at the sites and on the volunteers.

The volunteers remained in an air-conditioned room for 20 minutes before each measurement. One effected initial measurements, after 1, 4 and 8 hours from application of the product. The spectra of these sites with 20 volunteers were obtained.

Figure 3:
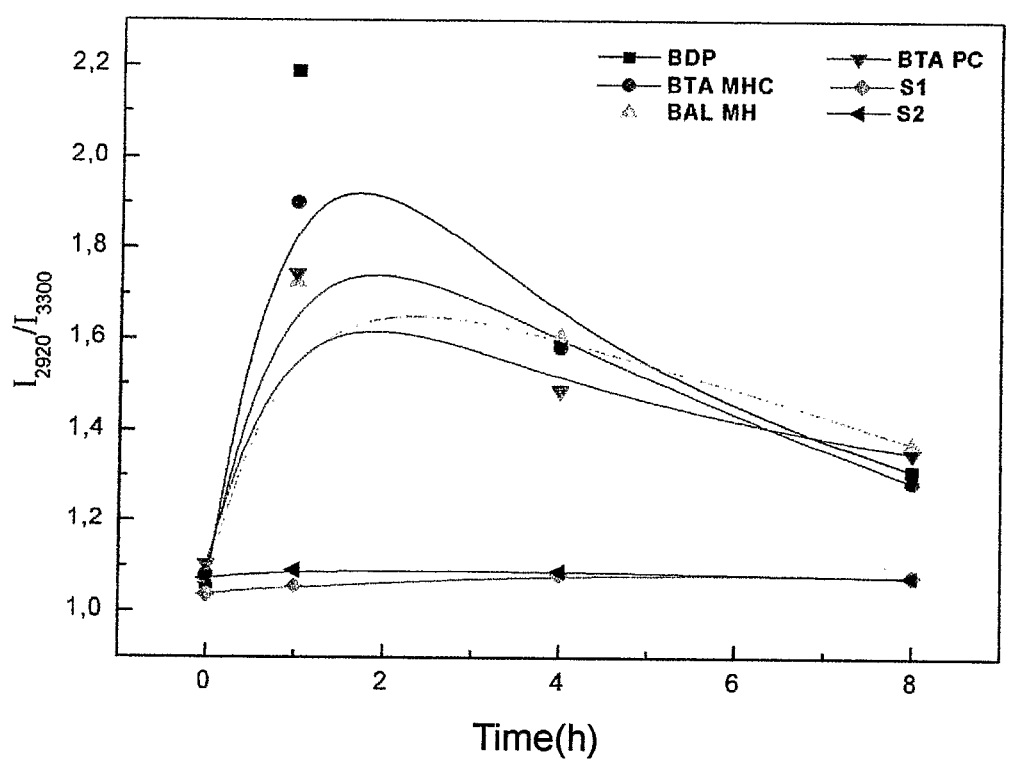
FIG. 3 is a graph representing the behavior of the compositions of the examples 1.1 and 1.2 in comparison with market products and control products along the time, with regard to the attribute moisturizing.

In FIG. 3 one can observe the behavior of the products studied along the time for the attribute of hydration, represented by the illustrated graph. The captions of the graph are:
BDP=control lipstick,
BTA PC=market lipstick,
BTA MHC=moisturizing lipstick
BAL MH=colorless moisturizing lipstick,
S1 and S2=controls Result: the product 1 applied to the forearm skin conferred statistically significant hydration in comparison with the treatment with control until 4 hours from application. On the other hand, the product 2 applied to the forearm skin conferred statistically significant hydration in comparison with the treatment with control until 8 hours from application.

3. Skin-Evaluation Test for Topical Compatibility

This study has the function of proving the absence of the potential of primary dermal irritation, accumulated dermal irritation and potential of dermal sensitization of the cosmetic composition of the present invention, represented by examples 1 and 1.2.

To carry out this test, 50 male and female volunteers, with 18 to 60 years of age were selected, excluding subjects that had diseases of the skin, injuries or nerves on the back and pregnancy or breast-feeding.

To carry out this study, the following material was used: semiocclusive dressings composed of 1.0-$cm^2$ filter paper discs duly identified, semi-permeable hypoallergenic sticking plaster for occlusion, physiological solution and samples of the cosmetic composition.

The following clinical researches were carried out:
I. Research for Primary Irritability 0.2 ml of the cosmetic composition was applied to each area of 1 $cm^2$ of the filter paper disc and a saline solution was applied to the control disc. These discs were fixed to the volar surface of the forearms of the volunteers with the aid of sticking plaster.

The patch test was removed by the researchers after 48 hours of contact with the skin, and the reactions were written down 30 minutes after removal, and then the reading of the region was effected. After 48 hours, new readings were effected.

II. Research for Accumulated Dermal Irritability

The sample was always applied to the same region, to the back, duly protected. Every 48 hours, the volunteers returned for removal of the dressings, reading of the sites and reapplication of the dressings to the same sites, for 3 weeks on end, in a total of 9 applications. The sample was reapplied to the skin always at the same place, and the reactions were written down.

III. Research for Dermal Sensitization

After the 9 consecutive applications, 2-week rest period followed, when no patch was applied. After this rest interval, one applied semiocclusive dressings containing the product under study and the control in a virgin area, that is to say, at a place where no patch had been applied. The test was removed by the researchers after 48 hours of contact with the skin, and the reactions were written down, 30 minutes after the removal. After another 24 hours, the last reading was effected.

Result: no potentials of primary dermal irritation, accumulated dermal irritation or dermal sensitization were observed.

The invention claimed is:

1. A non-rinse-off cosmetic product characterized in that it is in the form of a lipstick or gloss for the lips and in that it comprises an amount of ricinoleyl monomaleate triglyceride ranging from 0.01% to 15.00%, by weight, and an amount of cupuaçu butter ranging from 0.1% to 20.00%, by weight, all percentages based on the total weight of the product.

2. A cosmetic product according to claim 1, characterized by comprising an amount of ricinoleyl monomaleate triglyceride ranging from 2.0% to 7.0% by weight, based on the total weight of the product.

3. A cosmetic product according to claim 1, characterized by comprising an amount of cupuaçu butter ranging from 1.5% to 8.00% by weight, based on the total weight of the product.

4. A cosmetic product according to claim 1, characterized by comprising marine collagen microspheres in an amount ranging from 0.01% to 5.00% by weight, based on the total weight of the product.

5. A cosmetic product according to claim 1, characterized by comprising at least one sensorial-modifying agent that provides softness, smoothness and adequate texture to the skin in an amount ranging from 50% to 95% by weight, based on the total weight of the product.

6. A cosmetic product according to claim 5, characterized in that the sensorial-modifying agent is selected from: mineral, vegetable and synthetic waxes, liquid and solid polymers, rheology agent, esters with carbon chain of different sizes, alcohols and combination thereof.

7. A cosmetic product according to claim 1, characterized by comprising at least one film former in an amount ranging from 0.1% to 10.0% by weight, based on the total weight of the product.

8. A cosmetic product according to claim 7, characterized in that the film-forming agent is selected from: glyceryl abietate, glyceryl rosinate, variants and derivatives thereof and mixtures thereof.

9. A cosmetic product according to claim 1, characterized by comprising at least one sunscreen agent.

10. A cosmetic product according to claim 9, characterized by comprising a sunscreen system, which is a mixture of 2-ethyihexyl p-methoxy cinnamate, benzofenone-3 and micronized titanium dioxide.

11. A cosmetic product according to claim 4, characterized by comprising at least one sensorial-modifying agent that provides softness, smoothness and adequate texture to the skin in an amount ranging from 50% to 95% by weight, based on the total weight of the product.

12. A cosmetic product according to claim 11, characterized by comprising at least one film former in an amount ranging from 0.1% to 10.0% by weight, based on the total weight of the product.

13. A cosmetic product according to claim 12, characterized by comprising at least one sunscreen agent.

14. A cosmetic product according to claim 13, characterized by comprising a sunscreen system, which is a mixture of 2-ethylhexyl p-methoxy cinnamate, benzofenone-3 and micronized titanium dioxide.

15. A non-rinse-off lipstick or gloss for the lips comprising an amount of ricinoleyl monomaleate triglyceride ranging from 0.01% to 15.00%, by weight, and an amount of cupuaçu butter ranging from 0.1% to 20.00%, by weight, and marine collagen microspheres in amount ranging from 0.01% to 5.00%, by weight, all percentages based on the total weight of the product.

16. The non-rinse-off lipstick or gloss for the lips of claim 15, wherein the association of ricinoleyl monomaleate triglyceride and cupuaçu butter forms a gel lamellar structure, and wherein the gel lamellar structure when applied on damaged lips is capable of lip damage restoration by 38% to 54%.

* * * * *

UNITED STATES PATENT AND TRADEMARK OFFICE
CERTIFICATE OF CORRECTION

PATENT NO.       : 8,999,355 B2                                           Page 1 of 1
APPLICATION NO.  : 11/910495
DATED            : April 7, 2015
INVENTOR(S)      : Spina et al.

It is certified that error appears in the above-identified patent and that said Letters Patent is hereby corrected as shown below:

In The Claims

Column 12,
Line 18, "2-ethyihexyl" should read --2-ethylhexyl--.

Signed and Sealed this
Sixteenth Day of February, 2016

Michelle K. Lee
*Director of the United States Patent and Trademark Office*